United States Patent [19]

Dunn

[11] Patent Number: 4,715,711
[45] Date of Patent: Dec. 29, 1987

[54] MINIATURE SAPPHIRE ANVIL CELL FOR RESERVOIR FLUID PROPERTY STUDIES

[75] Inventor: Keh-Jim Dunn, Fullerton, Calif.

[73] Assignee: Chevron Research Company, San Francisco, Calif.

[21] Appl. No.: 10,601

[22] Filed: Feb. 4, 1987

Related U.S. Application Data

[63] Continuation-in-part of Ser. No. 789,058, Oct. 18, 1985, abandoned.

[51] Int. Cl.$^4$ .............................................. G01N 1/10
[52] U.S. Cl. ..................................... 356/246; 350/410
[58] Field of Search ................................ 356/246, 410

[56] References Cited

U.S. PATENT DOCUMENTS 4,602,377 7/1986 Schiferl et al. ...................... 378/150

OTHER PUBLICATIONS

American Institute of Physics Handbook, 3rd Ed., Dwight E. Gray, 1972, McGraw-Hill Inc., pp. 6–60.

*Primary Examiner*—Eugene R. LaRoche
*Assistant Examiner*—James C. Lee
*Attorney, Agent, or Firm*—S. R. La Paglia; E. J. Keeling; E. A. Schaal

[57] ABSTRACT

The present invention is a high-pressure sapphire cell designed to measure the properties of a petroleum reservoir fluid sample. It comprises at least two sapphire anvils, a pressure vessel having inlet and outlet parts, gaskets between the anvils and the pressure vessel; and a means for forcing the anvils together to form a fluid-tight seal between the anvils and the pressure vessel. Once a fluid sample enters the pressure vessel, a high pressure environment similar to a petroleum reservoir is created by an outside pressure pump via a pressure inlet tube. It is in this state that the fluid measurements are made on the sample.

3 Claims, 4 Drawing Figures

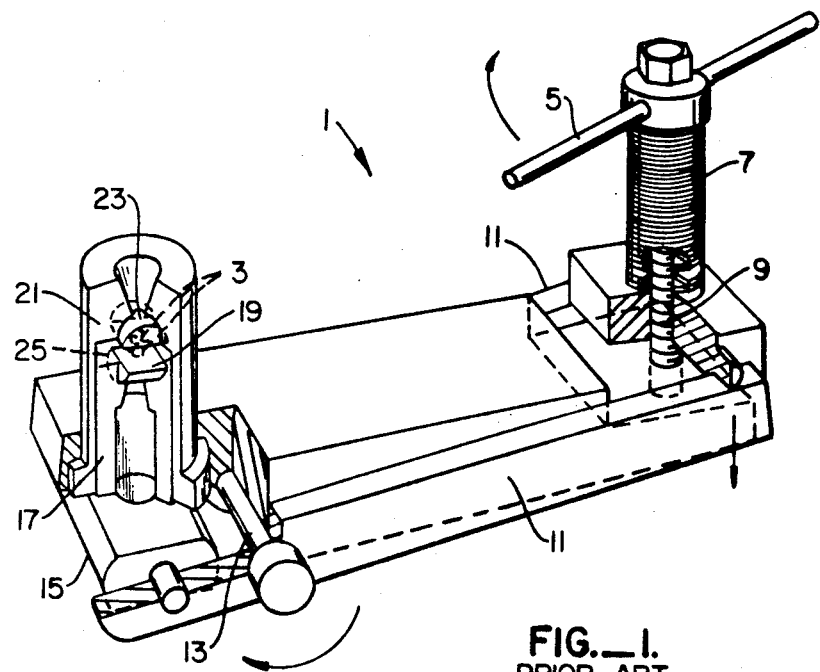
FIG._1.
PRIOR ART
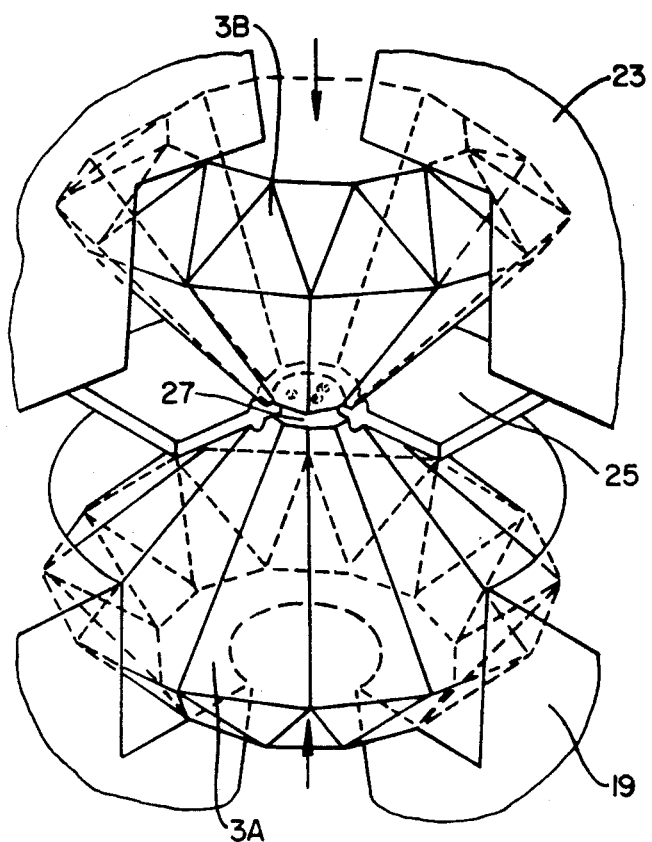
FIG._2.
PRIOR ART

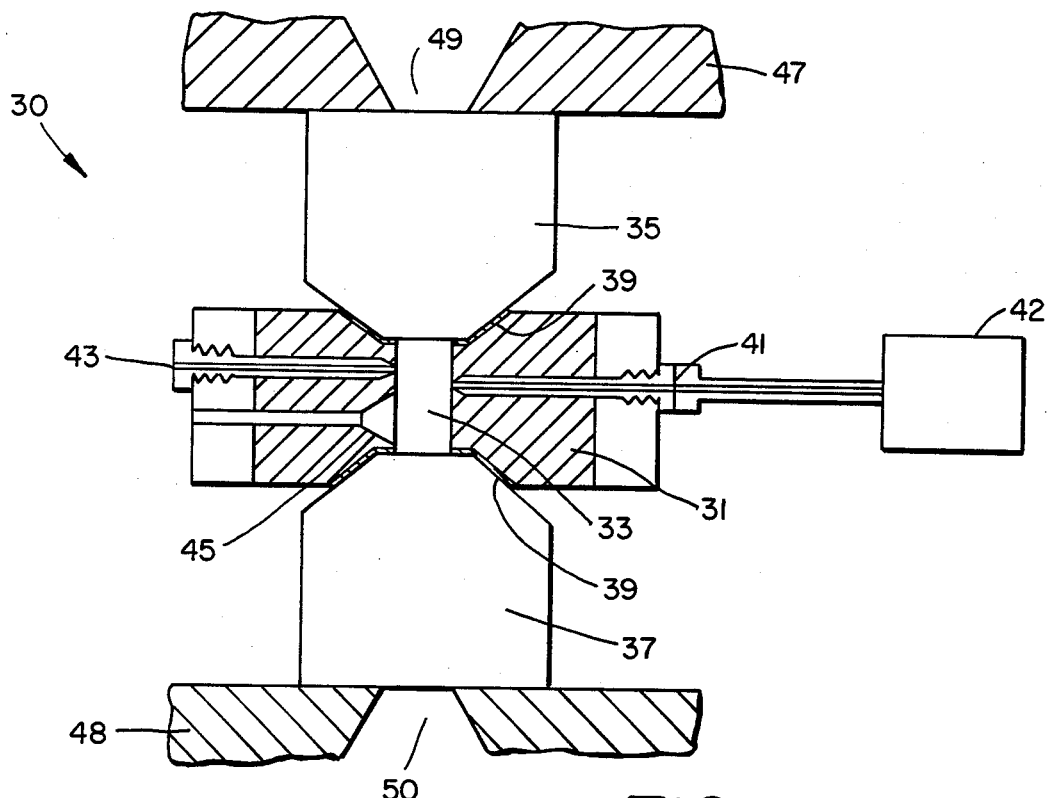
FIG_3
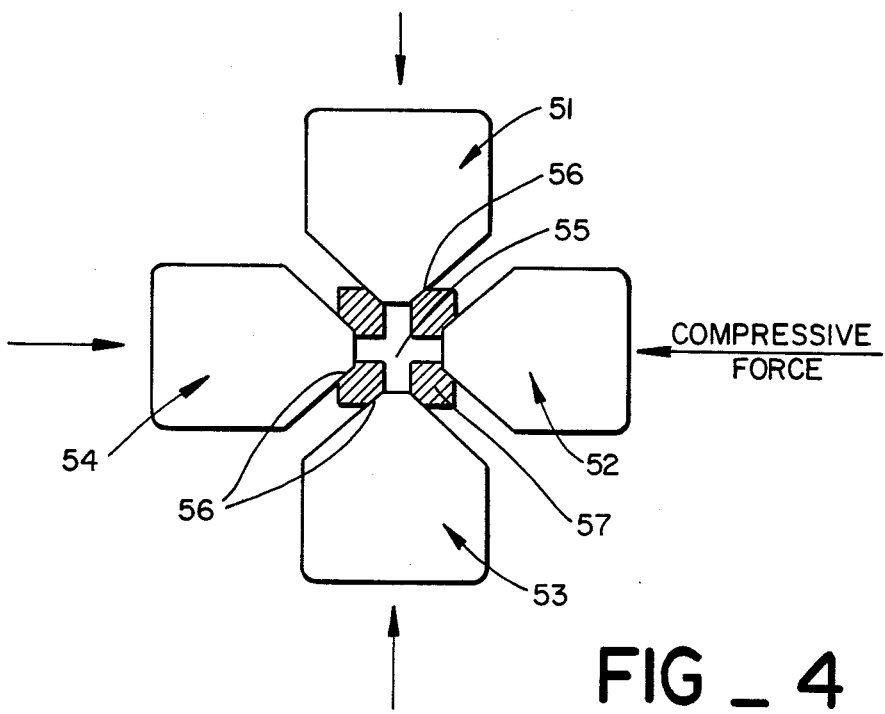
FIG_4

MINIATURE SAPPHIRE ANVIL CELL FOR RESERVOIR FLUID PROPERTY STUDIES

This application is a continuation-in-part of application U.S. Ser. No. 789,058, filed Oct. 18, 1985 now abandoned.

BACKGROUND OF THE INVENTION

1. Field of the Invention

This invention generally relates to devices that measure fluid properties. Here, the present invention is used to simulate the reservoir conditions of pressure and temperature and to measure fluid properties within a sample.

2. Background Information

The high-pressure, visual cell is a very useful device in the petroleum industry. It is used to simulate the underground reservoir conditions of pressure (P) and temperature (T), to measure fluid properties such as density, viscosity and interfacial tension, etc., as well as in situ visual observation of the test specimen. This information is very important for the optimization of production from such reservoirs.

The existing industrial equipment for measuring fluid properties is generally limited to pressures of 70-80 MPa (10.2-11.6 kpsi) and temperatures of 150° C. (302° F.) and is useful for simulating reservoir conditions with pressures and temperatures less than the specified limits. However, recent discoveries have found reservoirs with pressures up to 18,000 psi (124 MPa) and temperatures up to 370° F. (188° C.). Obviously, for accurate measurements, the existing equipment is not adequate for the higher temperatures and pressures.

Most of these existing visual cells have a typical sample volume of 50 cc (1" diameter and 7" long cell). Frequently, the samples are transferred via a sample retrieving tube to other devices that are held at the same P/T condition and which measure density, viscosity and interfacial tension, etc. Such procedures are usually time consuming, and in many cases, the experimental conditions are not completely identical to each other. Furthermore, the massive equipment that have large samples under compression store a considerable amount of energy which creates a hazardous condition. These hazards require extra safety shields to protect the equipment operators from being injured.

Looking into the future, there is a need to improve the system for measurements of the fluid properties. The continuing evolution will involve: miniaturizing equipment and samples to reduce the problems inherent in constructing massive equipment and preparing large samples, measuring with nondestructive methods to prevent altering the overall composition of the fluids, increasing accuracy and efficiency of the experimental measurements, and reducing the time required and cost involved in all of these operations.

The general idea is to have a small pressure cell that is capable of measuring everything in a short time. The present invention addresses such a challenge by proposing a conceptual design of a miniature high-pressure, visual cell combining all the measuring devices into just one probe; i.e., a laser beam of suitable frequency for measuring all quantities of viscosity, interfacial tension, density, and equation of state of the fluids.

The present proposed design of the miniature visual cell for petroleum reservoir fluid studies is inspired from the diamond anvil press now widely used in the high-pressure research community. A typical diamond press is shown in FIG. 1. It consists of two brilliant cut single crystal diamond anvils with metal gaskets sandwiched in between them. The sample chamber is typically several hundred microns ($\mu$m) diameter and 20-100 $\mu$m thick. Such a press or press of similar design was first used by Van Valkenburg [A. Van Valkenburg, in "High Pressure Measurement" pp. 87-84, ed. by A. Giardini and E. C. Lloyd, Butterworth, Washington (1963)] and others [C. E. Weir, E. R. Lippincott, A. Van Valkenburg, and E. N. Bunting, A 63 J. Res. Natl. Bur. Stand. Sect. p. 55 (1959), see also Weir et al., U.S. Pat. No. 3,079,505]. Later, Piermarini et al. [G. J. Piermarini, R. A. Forman, and S. Block, Rev. Sci. Instrum. 49, p. 1061 (1978)] showed that the ruby fluorescence shift induced by pressure can be used as a secondary pressure scale up to 300 kbar ($4.3 \times 10^6$ psi), and Mao and Bell [H. K. Mao and P. M. Bell, Science 191, p. 851 (1976), Xu et al., Science 232, p. 1404 (1986), see also Bell et al., U.S. Pat. No. 4,339,252] further extended the pressure capability to over 1 Mbar ($14.5 \times 10^6$ psi). In the last three to four years, the diamond press has become a very popular tool in the high pressure research community for X-ray diffraction, optical (Raman and Brillouin), resistivity and magnetic studies for various physical phenomena such as phase transformation, reaction kinetics, electron and phonon transport properties and superconductivity, etc. For a general discussion on this subject, see A. Jayaraman, The Diamond-Anvil High-Pressure Cell, Sci. Amer. 250, 54 (April 1984).

Of course, such a design will not be suitable for petroleum reservoir fluid studies because the fluid sample needs to be transferred under pressure and the chamber volume of the diamond press is too small. The general approach of the present invention is to use the sapphire anvils instead of the diamond anvils, and to scale up the cell size with a volume of approximately several cubic centimeters. This is suitable for the sample transfer and all the required measurements, but yet it is ten times smaller than the conventional visual cell.

BRIEF DESCRIPTION OF THE DRAWINGS

FIG. 1 (Prior Art) is a view of a high-pressure diamond cell device;

FIG. 2 (Prior Art) is an enlarged view of the opposing diamonds in the device of FIG. 1;

FIG. 3 is a cross-sectional view of a dual sapphire anvil cell; and

FIG. 4 is a cross-sectional view of a multiple sapphire anvil cell.

DETAILED DESCRIPTION OF THE INVENTION

As mentioned in the Background Information section, FIGS. 1 and 2 are representations of a Diamond Anvil High-Pressure Cell [see A. Jayaraman, Sci. Amer. 250, 54 (April, 1984)]. It is helpful to illustrate this device to understand the present invention, however, care must be taken not to equate the two as there are some major differences, one of them being the sizes and capabilities involved.

FIG. 1 shows the overall thrust mechanism 1 which serves to generate the force on a set of two diamond anvils 3 (a similar device is shown in U.S. Pat. No. 3,079,505). The device operates in a similar manner to a nutcracker and is as follows. A handle 5 is turned clockwise on a pressure bolt 9 having springs 7 which force a lever arm 11 to turn on a fulcrum 13. The lever arm 11 transmits force to a piston pressure plate 15 and then to a piston 17 which houses a lower piston rocker 19 that is used to support a lower diamond 3A for the diamond anvil 3. A piston plate 21 supports an upper piston rocker 23 that fixes an upper diamond 3B. As shown in FIG. 2, the two diamonds 3A and 3B comprise the diamond anvil set 3 and are "brilliant cut" with their points removed so that each has a flat face. The flat face of each diamond is fit against the other and a gasket 25 is placed between them. The gasket 25 is the definition for a cell 27 in which the sample is placed and the cell 27 is formed by drilling a small hole in the gasket material (i.e., steel) and compressing the opposing diamond faces together. Normally, the cell 27 is a cylinder 200 micrometers across and is approximately 100 micrometers deep.

Referring now to the present invention, FIG. 3 shows an example of a sapphire anvil cell 30. It consists of a belt-type pressure vessel 31 (i.e., cylindrical) made of hard metal alloys (such as Incoloy alloy 903, made by Huntington Alloys, Inc., Huntington, W. Va.) with a cylindrical sample space 33 in the center. There are two truncated conical sapphire anvils, 35 and 37, with flat opposing faces on each side of the vessel 31. The axes of the upper sapphire anvil 35 and the lower sapphire anvil 37 are chosen to be along the hard crystallographic direction. The fluid-tight seal at both ends of the vessel 31 is accomplished by applying compressive force on both the upper 35 and lower 37 anvils with a gasket 39 (soft metals or strong polymeric materials) between each anvil and the pressure vessel 31. The applied force will normally exceed the yield point of the gasket 39 so that a perfect seal is formed. There are pressure tube inlets 41 and outlets 43 for sample transfer and pressurization. Sapphire windows 45, if needed, can be placed on the cylindrical wall of the vessel 31 for visual inspection. An upper pushing block 47, with an aperture 49, and a lower pushing block 48, with an aperture 50, transfer the force from some outside pressure means to the sapphire anvils 35 and 37 and the pressure vessel 31. The apertures 49 and 50 are provided for access by a laser beam for photon correlation spectroscopy, Brillouin scattering or other measurements (such as laser excitation of a ruby to determine pressure). The petroleum reservoir fluid to be studied can be transferred through the pressure tube inlet 41 to fill the sample chamber 33. Once the chamber is filled, the pressure outlet 43 can be closed. The pressure in the sample chamber can be generated by an outside displacement pump 42 (such as the FDS 510 displacement pump of Core Research Inc.) connected to pressure tube inlet 41. Thus, unlike the prior art devices, the pressure in the chamber is created by an outside source and not by bringing the sapphire anvils together.

Another possible design is the multiple sapphire anvil cell shown in FIG. 4. It consists of four to six sapphire anvils 51, 52, 53, 54 surrounding a sample chamber 55. Again, there are gaskets 56 between the anvils 51, 52, 53, 54 and a pressure vessel 57. However, even though this design provides more optical access to the sample chamber 55, it is not as simple as the dual sapphire anvil cell. Many different versions can be derived from these two basic designs, and details can be worked out depending upon the experimental objectives.

The major objectives in the measurements of petroleum reservoir fluid properties are to find out the composition, density, viscosity and interfacial tension of the fluids at the reservoir's P/T conditions. As we know, when a laser beam of suitable frequency is passed through the aperture 49 (or 53 in FIG. 4), the sapphire 35 (or 37) (or 51, 52, 53 and 54 in FIG. 4), into the sample chamber 33 (or 55 in FIG. 4), the photon correlation spectroscopy method can be used to determine the viscosity and interfacial tension of the reservoir fluid. For example, at any temperature above absolute zero, random thermal processes generate surface fluctuations of low amplitude (so-called surface capillary waves) at the interface between two fluid phases (liquid-vapor or liquid-liquid). The frequency and the decay time of these fluctuations are controlled by the interfacial tension, the density and the viscosity of the two phases. The scattered light of a focused laser beam impinging on the surface carries this information. Once the measurement has been made, the results can be recorded and analyzed to deduce the values of the interfacial tension and viscosity.

The very same laser beam can also be used to determine the sound velocity of the fluids from the Brillouin shift. For example, when a laser light of wavelength $\lambda_o$ is incident on a medium of refractive index n, and is scattered through an angle $\theta$ away from the incident beam, the scattered light suffers a frequency shift $\Delta f$ by giving or taking energy away or from an acoustic wave in the medium. The velocity of this acoustic wave $v$ is given by $$v = \frac{\lambda_o |\Delta f|}{2n \sin(\theta/2)}$$

This is commonly known as Brillouin Scattering.

The density versus pressure may also be deduced from the acoustic velocity information. In a liquid, since the shear modulus is zero, the isothermal bulk modulus K is simply given by $K = \rho v^2$, where $\rho$ is density and $v$ is fluid velocity. K is defined as $$K = -V \frac{dP}{dV} = \rho \frac{dP}{d\rho}$$

where V is volume and P is pressure. So that we get $$\int_{\rho_o}^{\rho} d\rho = \int_o^P \frac{dP}{v^2}$$

Therefore, after obtaining the fluid velocity as a function of pressure, the density versus pressure relation may be deduced.

The determination of the acoustic velocity of the fluid can also be accomplished by measuring the transit time of ultrasonic waves through the fluid volume. Employing ultrasonic techniques to the present proposed system is quite straightforward, one can either use a pulse-echo (one transducer is bonded to the back face of one of the sapphire anvils) or a transmitted wave technique (two transducers are used, one on the back face of each sapphire anvil) to obtain the sound velocity of the fluid, assuming the sound velocity in the sapphire is known. The accuracy of this kind of measurement is normally one part in $10^4$.

A miniature visual cell is the future direction in the development of better devices for the measurements of petroleum reservoir fluid properties. The present design of sapphire anvil cells coupled with the photon correlation spectroscopy and ultrasonic techniques should be a plausible way to solve the problem.

Since many modifications and variations of the present invention are possible within the spirit of this disclosure, it is intended that the embodiments disclosed are only illustrative and not restricted. For that reason, reference is made to the following claims rather than to the specific description to indicate the scope of this invention.

What is claimed is:

1. A high-pressure cell for measuring the properties of a petroleum reservoir fluid sample, comprising:
    two truncated, essentially conical, transparent sapphire anvils having opposing flat surfaces, said anvils being aligned on the same lengthwise axis;
    a pressure vessel for containing a sample under high pressure having an inner chamber with an opening at each end of said pressure vessel, said pressure vessel being located between said sapphire anvils such that the opposing surfaces of said sapphire anvils are placed over said openings to form a high-pressure fluid-tight seal;
    gaskets located between said anvils and said pressure cell to ensure a pressure and fluid tight seal, wherein said gaskets are made a material selected from the group consisting of soft metals and strong polymeric materials, said seals being formed by the yield point of said gaskets being exceeded by the compressive forces that the sapphire anvils exert on said pressure cell;
    a high-pressure inlet connected to said pressure vessel to admit a sample under high pressure;
    a high-pressure pump operably connected to said high-pressure inlet;
    a high-pressure outlet connected to said pressure vessel to remove said pressurized sample; and
    a pushing block located at the base of at least one sapphire anvil, said block having an aperture in the area adjacent to the sapphire anvil such that light may pass through the aperture in the block, the sapphire anvil, and the pressure vessel.

2. The apparatus as described in claim 1 in which a window is placed in the pressure vessel for visual inspection.

3. A method for measuring the properties of a fluid sample, comprising:
    flowing a petroleum reservoir sample under pressure to a sample chamber;
    applying pressure on said sample by an outside pressure pump via a pressure inlet tube; and
    measuring the properties of the petroleum reservoir fluid sample through said at least one sapphire anvil.

* * * * *